US006480561B2

(12) United States Patent
Proksa

(10) Patent No.: US 6,480,561 B2
(45) Date of Patent: Nov. 12, 2002

(54) COMPUTED TOMOGRAPHY METHOD FOR FORMING A SCANNOGRAM

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/759,178

(22) Filed: Jan. 12, 2001

(65) Prior Publication Data

US 2001/0031032 A1 Oct. 18, 2001

(30) Foreign Application Priority Data

Jan. 15, 2000 (DE) .......................................... 100 01 492

(51) Int. Cl.⁷ .............................................. A61B 6/00
(52) U.S. Cl. .......................................... 378/16; 378/15
(58) Field of Search ........................... 378/16, 108, 15, 378/20

(56) References Cited

U.S. PATENT DOCUMENTS 5,400,378 A  *  3/1995  Toth ............................. 378/16
5,412,702 A  *  5/1995  Sata ............................... 378/4
5,541,971 A  *  7/1996  Saito ............................ 378/15

FOREIGN PATENT DOCUMENTS

DE           4103588           5/1992

OTHER PUBLICATIONS

Image Processing for Computer–Aided Diagnosis of Lung Cancer by CT (LSCT) by Shinji Yamamoto et al., in Systems and Computers in Japan, vol. 25, No. 2, (1994), pp. 67–80.
"Computer tomography method involving helical scanning of an examination zone" by Per–Erik Danielsson, filed Sep. 10, 1999, U. S. Ser. No. 09/380972.

* cited by examiner

Primary Examiner—Robert H. Kim
Assistant Examiner—Jurie Yun
(74) Attorney, Agent, or Firm—John Vodopia

(57) ABSTRACT

The invention relates to a method of forming a scannogram for a computed tomography apparatus. During the acquisition of the measured values for the scannogram, the scanning unit or the radiation source rotates about the examination zone and a 3D data set is reconstructed from the measured values acquired during the acquisition. A synthetic projection image which acts as the scannogram can be calculated from such a 3D data set.

7 Claims, 3 Drawing Sheets

COMPUTED TOMOGRAPHY METHOD FOR FORMING A SCANNOGRAM

Figure 1:
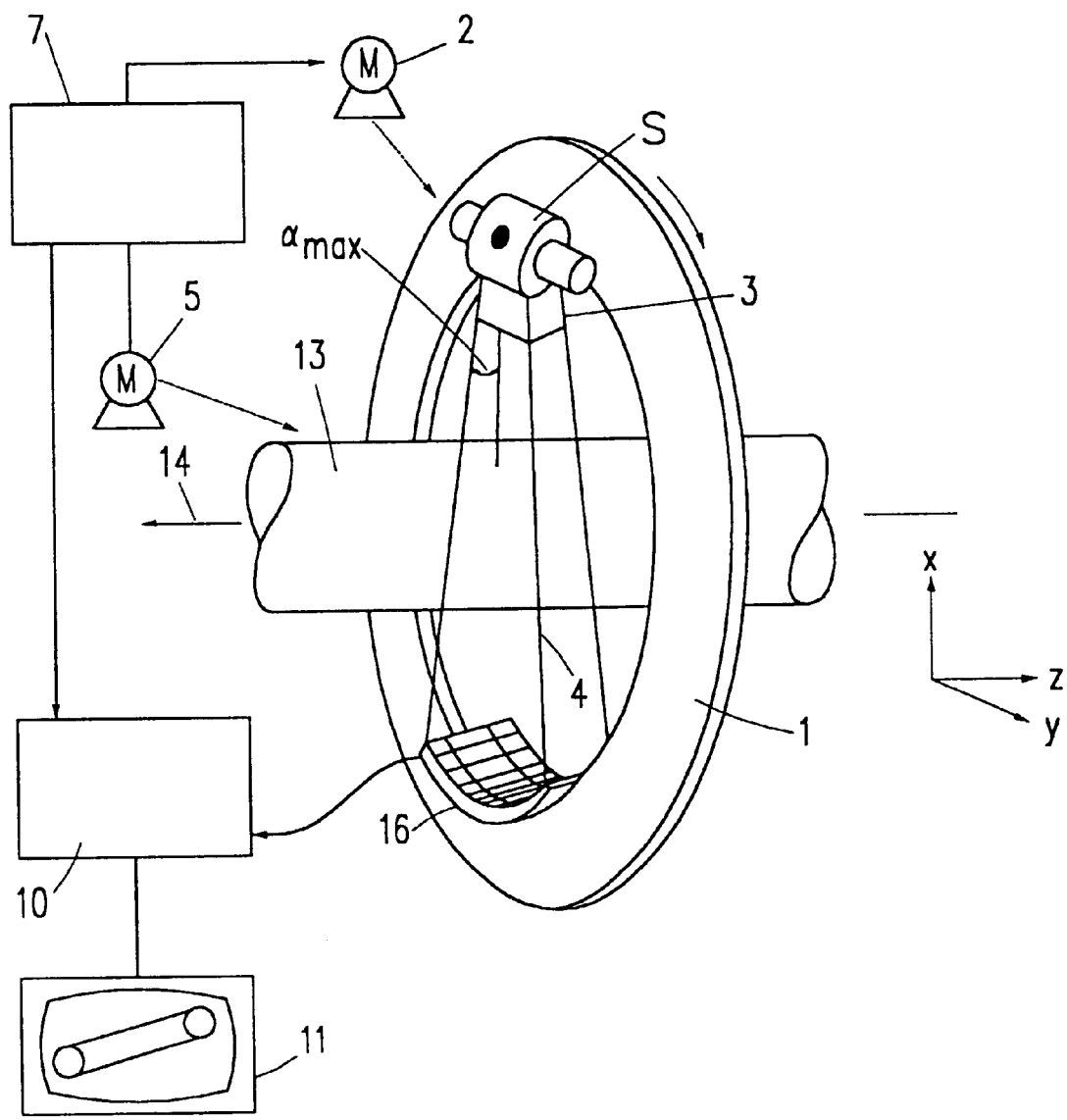

The invention relates to a computed tomography method for forming a scannogram by means of a computed tomography apparatus which includes a scanning unit for the acquisition of measured values that is rotatable about an axis of rotation and is provided with a radiation source and a detector unit, a relative motion which includes a displacement in the direction parallel to the axis of rotation taking place between the scanning unit and an examination zone during an acquisition of measured values, followed by the extraction of a scannogram from the measured values. The invention also relates to a computed tomography apparatus which is suitable for carrying out such a method, and to a computer program for controlling a computed tomography apparatus in conformity therewith.

It is known that a scannogram of an examination zone is formed in that a relative motion occurs between the examination zone and the scanning unit during the acquisition of the measured values, which relative motion includes merely a translation in the direction parallel to the axis of rotation. The measured values thus relate to line-shaped or strip-shaped sections of the examination zone which are combined so as to form a two-dimensional image or scannogram. The amount of calculation work required for such a scannogram is small in comparison with that required for the reconstruction of a computer tomogram. The dose required for forming a scannogram of adequate image quality is significantly smaller than the dose that would be required for the reconstruction of the attenuation in a section of the same length by means of the customary CT methods (CT=Computed Tomography). Therefore, scannograms are customarily used to define the region (shortened in comparison with the scannogram) which is of interest to the diagnosis and is to be imaged by means of a CT method.

Conventional scannograms, however, have limitations in that the direction wherefrom the examination zone is irradiated is predetermined as well as the projection geometry which is imposed by the distance between the radiation source and the detector unit. Therefore, during the formation of a scannogram it may occur that the region in the scannogram which is important to the diagnosis cannot be recognized, for example because it is masked by a bone structure. It is an object of the present invention to provide an essentially more flexible method of forming a scannogram.

This object is achieved by taking the following steps:
rotating the scanning unit about the axis of rotation during the acquisition of the measured values,
reconstructing from the measured values a 3D data set which is three-dimensionally dependent on the attenuation of the radiation in the examination zone covered by the scanning unit,
calculating at least one synthetic projection image from the 3D data set.

At the first glance it seems like a paradox to derive the measured values for a scannogram by making, like during the actual CT examination, the scanning unit rotate about the axis of rotation during the data acquisition and by reconstructing the attenuation in the examination zone by way of a comparatively intricate reconstruction method, thus yielding a 3D data set. These steps are also carried out during the actual CT examination, so that the question arises why the regions of interest for the diagnosis (ROI) for the subsequent CT method should be defined on the basis of a scannogram whose formation also requires the execution of a CT method, that is, even for a more extensive region in most cases. Moreover, it is also necessary to derive a synthetic projection image which serves as a scannogram from said 3D data set. The term "synthetic" is used for the projection image in this context because it is not formed directly like a scannogram but must be calculated from the previously reconstructed 3D data set.

The invention is based on the recognition of the fact that the 3D data set required for the formation of a scannogram can be acquired while using a dose which is not larger than that used for a conventional formation of a scannogram. This dose is significantly smaller than the dose required for the actual CT examination of a section of the same length, so that the attenuation in the individual voxels of the examination zone can be reconstructed with a very poor signal-to-noise ratio only. However, because the image value for each pixel in the scannogram is derived from a plurality of voxels of the examination zone, an adequate signal-to-noise ratio will be obtained for the scannogram derived from said data set. Consequently, the dose will not be higher than during a conventional formation of a scannogram.

The choice of the projection geometry is completely free. For example, the scannogram can be derived from the 3D data set by parallel projection for which voxels situated on parallel rays are taken into account for calculating the image value in the pixel in which the relevant ray terminates. Projection images can be formed with a projection direction that can be chosen at random, that is, also with a projection direction which is not perpendicular (oblique) relative to the axis of rotation. The projection geometry need be fixed only after the acquisition of the measured values for the 3D data set and a plurality of different scannograms can be derived from one 3D data set without it being necessary to acquire measured values again while exposing the patient to a further radiation dose.

A CT method must be suitable for the examination of heavy as well as thin patients. If the examination of all patients were performed with always the same radiation intensity and the same radiation quality, either an excessively high radiation dose would be applied in the case of a thin patient or an inadequate signal-to-noise ratio would be obtained in the event of a heavy patient. The version disclosed in claim 2 enables preselection of the radiation quality and/or radiation intensity for a subsequent CT examination in such a manner that there is no unnecessary radiation load and that an adequate signal-to-noise ratio is ensured.

Even when such an adaptation to the relevant patient has been performed, problems may arise due to the fact that in the case of lateral irradiation the attenuation is stronger than in the case of irradiation from the front (a.-p.), so that either the radiation load becomes too high for one irradiation direction or the signal-to-noise ratio becomes too poor for the other irradiation direction when a patient is examined with a constant radiation intensity and a constant radiation quality. Such problems can be avoided by means of the version of the invention as disclosed in claim 3; this version enables a given signal-to-noise ratio to be obtained with an as small as possible radiation load for all irradiation directions, i.e. for all positions of the scanning unit.

In such a computed tomography apparatus the measured values could in principle be acquired by making the scanning unit rotate in a given position so as to acquire the measured values for the reconstruction of a slice or layer, followed by displacement of the scanning unit in a direction of the axis of rotation so as to acquire the measured values for a neighboring slice, etc. The helical relative motion disclosed in the further version of claim 5, where rotation and displacement take place continuously, however, is more advantageous because it involves a smooth transition from one radiation source position to the next.

Claim 6 describes an attractive further embodiment of the computed tomography apparatus. Granted, the scannogram could also be formed by means of a computed tomography apparatus in which the radiation source emits a fan-shaped radiation beam (fan beam) and the detector unit comprises only a single line, but the embodiment according to claim 6 enables faster acquisition of the measured values.

Claim 7 describes the software for the control unit of the computed tomography apparatus whereby the method according to the invention can be carried out.

Figure 2:
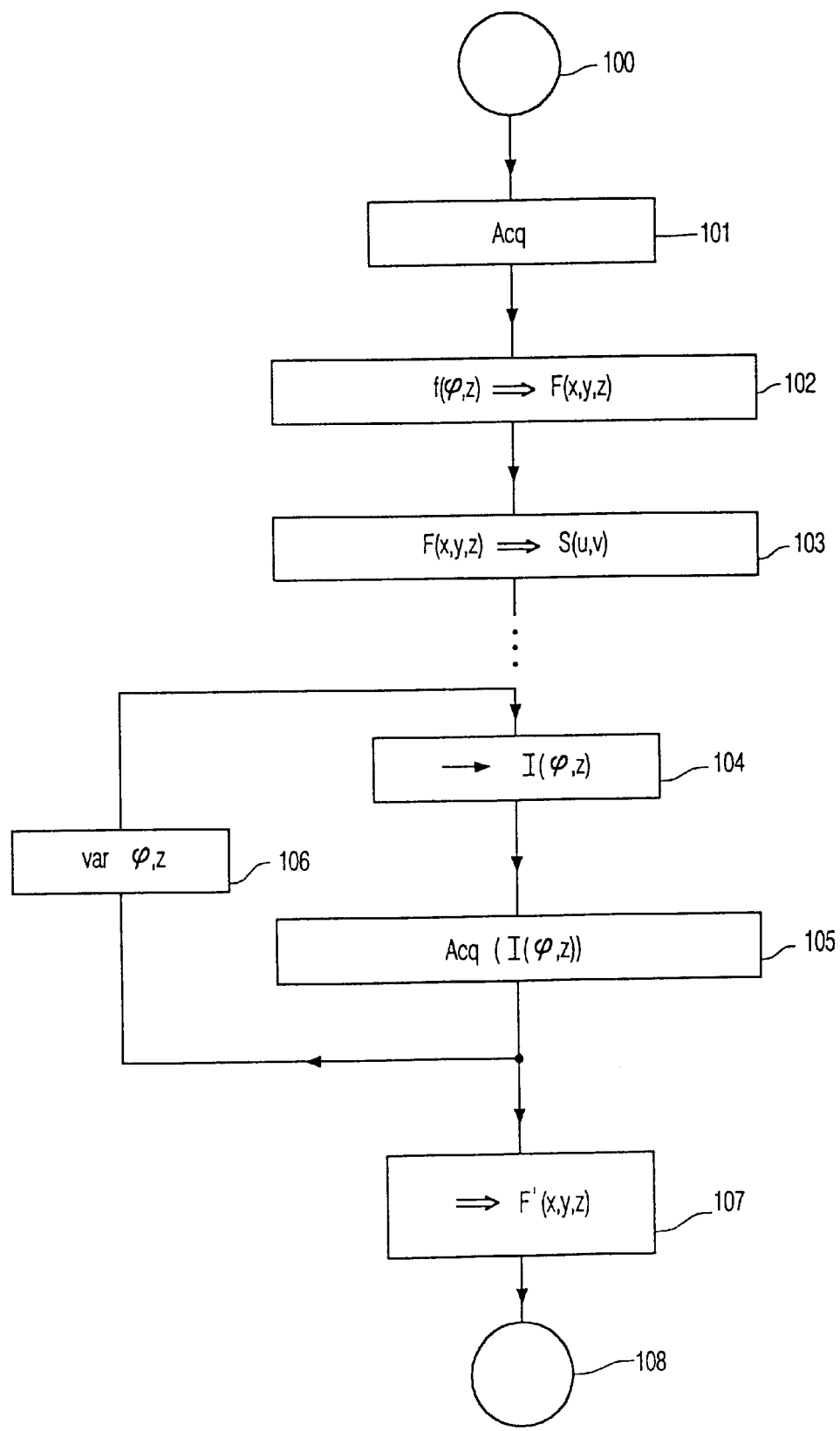
Figure 3:
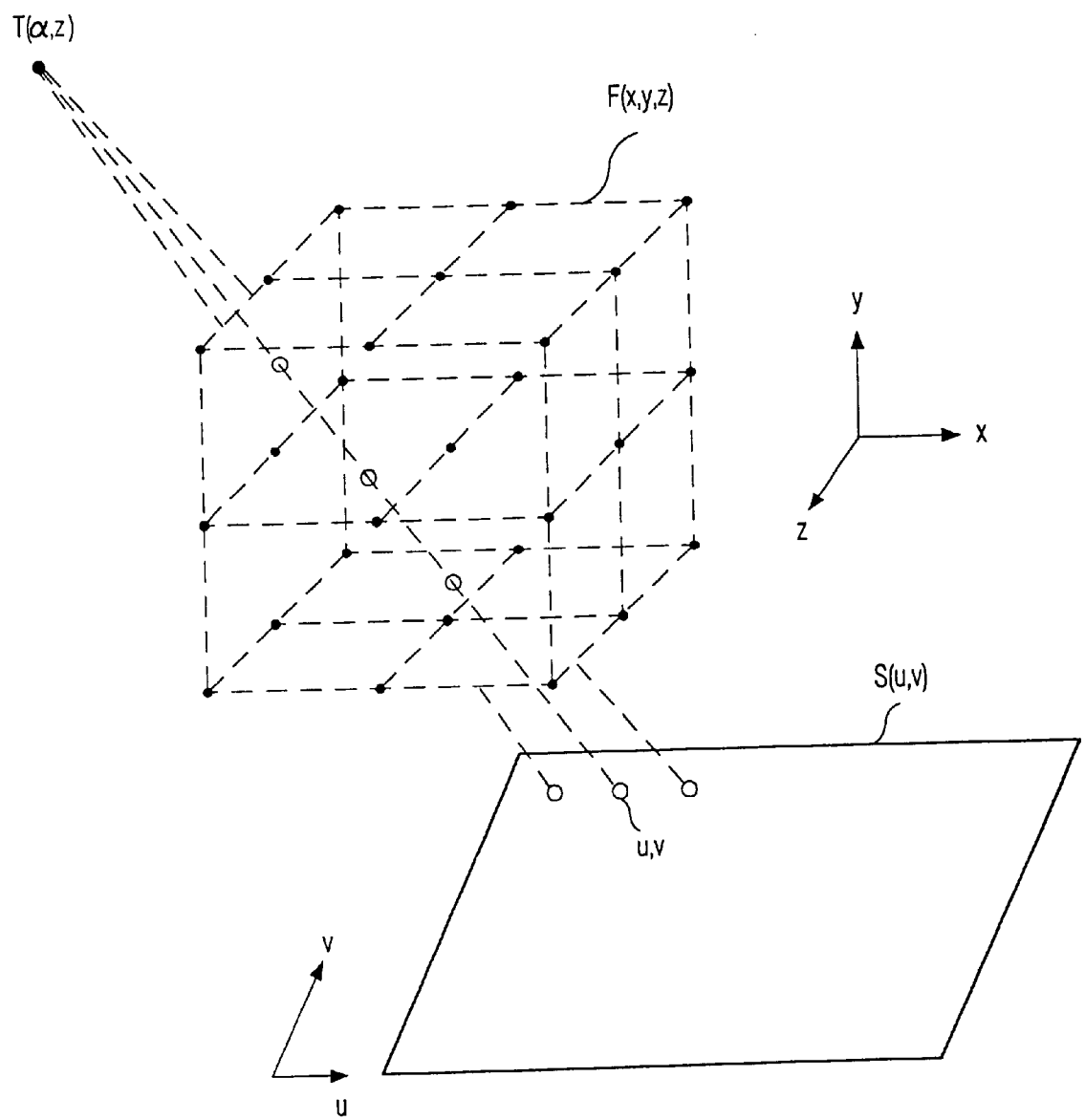

The invention will be described in detail hereinafter with reference to the drawings. Therein:

FIG. 1 shows a computed tomography apparatus which is suitable for carrying out the method according to the invention, FIG. 2 shows a flow chart of an examination procedure carried out by means of such a computed tomography apparatus, and FIG. 3 illustrates the formation of a synthetic projection image from a 3D data set.

The computed tomography apparatus shown in FIG. 1 includes a scanning unit in the form of a gantry 1 which is capable of rotation about an axis of rotation 14. To this end, the gantry is driven at a preferably constant but adjustable angular speed by a motor 2. On the gantry 1 there is mounted a radiation source S, for example, an X-ray source. The X-ray source is provided with a collimator arrangement 3 which forms a conical radiation beam 4 (cone beam) from the radiation produced by the radiation source S, that is, a radiation beam having a finite dimension other than zero in a plane perpendicular to the axis of rotation as well as in the direction of the axis of rotation.

The radiation beam 4 irradiates an examination zone 13 in which a patient arranged on a patient table may be present (both not being shown). The examination zone 13 is shaped as a cylinder. After having traversed the cylinder, the X-ray beam 4 is incident on a two-dimensional detector unit 16 which is attached to the gantry 1 and comprises a plurality of detector elements which are arranged in the form of a matrix. Each detector element is capable of supplying a measured value for a ray of the radiation beam 4 in each radiation source position. The detector elements are arranged in rows and columns. The detector columns extend parallel to the axis of rotation and the detector rows may lie in planes perpendicular to the axis of rotation, for example on an arc of a circle around the radiation source S. The detector rows usually comprise significantly more detector elements (for example, 1000) than the detector columns (for example, 16).

The angle of aperture $\alpha_{max}$ of the radiation beam 4 (the angle of aperture is to be understood to mean the angle enclosed by a ray of the beam 4 which is situated in a plane perpendicular to the axis of rotation 14 and at the edge of the radiation beam, relative to a plane defined by the radiation source S and the axis of rotation 14) then determines the diameter of the cylinder in which the object to be examined must be present during the acquisition of the measured values. The object to be examined, or the patient table, can also be shifted parallel to the direction of the axis of rotation 14 by means of a motor 5. The speed of this displacement is preferably constant and adjustable. When the two motors 2 and 5 operate simultaneously, the radiation source and the detector unit 16 will perform a helical scanning motion.

The measured data acquired by the detector unit 16 on the rotating gantry 1 is applied to an image processing computer 10 which is usually situated at a fixed point in space and is connected to the detector unit via a wireless data slip ring (not shown). A control unit 7, in communication with the image processing computer 10, controls motors 2 and 5. The image processing computer 10 is capable of performing various image processing operations and for displaying acquired and processed images upon a display 11. It is inter alia capable of reconstructing the attenuation of the X-rays in the examination zone 13 from the acquired measured data, thus yielding a 3D data set; on the other hand it is also capable of deriving from said 3D data set synthetic projection images which serve as a scanogram.

The method according to the invention will be described in detail hereinafter on the basis of the flow chart shown in FIG. 2. After the initialization in the block 100, the measured values are acquired in the block 101. To this end, the motors 2 and 5 are switched on so that the gantry rotates about the examination zone 13 and the patient table with the patient arranged thereon is displaced in the direction parallel to the axis of rotation 14, that is, in the z direction of the Cartesian co-ordinate system shown. The radiation source is switched on at the same time, that is, with an intensity which is significantly lower than that used during the later CT examination. In each radiation source position (defined by the position $\phi$ of the radiation source S relative to the axis of rotation 14 or the z co-ordinate of the table top) the detector unit 16 supplies a set of measured values $f(\phi,z)$ which represent the integral of the attenuation along the individual rays of the radiation beam S through the examination zone.

After such an acquisition of the measured values the absorption distribution in the examination zone is reconstructed in the step 102. The attenuation of the radiation in the individual voxels of the examination zone 13 (defined by their position x, y, z) is then reconstructed from the measured values which represent the line integral of the attenuation along the relevant ray. This yields a 3D data set $F(x, y, z)$. A suitable reconstruction method is described in PCT/IB 99/00027 (PHQ 98-020). Therein, only the measured values acquired while the radiation source irradiates the relevant voxel from an angular range of exactly 180° (related to the relevant voxel) are acquired or taken into account for the reconstruction for each voxel. The known method enables the reconstruction to commence already prior to the completion of the acquisition of the measured values in the step 101.

During the next step 103 a scannogram $S(u,v)$ is calculated from the 3D data set $F(x,y,z)$ reconstructed in the step 102, that is, a two-dimensional synthetic projection image is calculated. This operation will be described in detail hereinafter with reference to FIG. 3. The examination zone for which the 3D data set is reconstructed is defined therein by a cube with a Cartesian grid whose grid points, symbolized by a solid dot (●), represent the voxels of the examination zone or the center of these voxels.

The scannogram is formed by projecting the reconstructed examination zone on a surface from a projection origin $T(\alpha,z)$ that can be chosen at random. To each pixel u, v in this scannogram there is assigned an image value which is dependent on the attenuation values along the ray in the examination zone which connects the relevant pixel u, v to the projection origin $T(\alpha,z)$. For one of these rays within the examination zone there are indicated ray points which are symbolized by a "hollow dot" (○) and are situated at regular distances. When a ray point coincides with a voxel, it is assigned the attenuation value determined for the relevant voxel. Otherwise the ray point is assigned an attenuation value which results from cubic interpolation of the attenuation values of the voxels neighboring the relevant ray point.

The image value at the pixel associated with the relevant ray can be determined, for example by summing the attenuation at the ray points or by weighted summing. However, the maximum value of the attenuation along the ray can also be taken into account or a value which can be determined by means of the customary so-called "volume rendering" methods.

Moreover, the scannogram is also determined by the projection geometry, that is, by the position of the projection point T(x,z) and the scannogram S(u,v) relative to the examination zone. For example, if the projection origin were shifted to infinite, a parallel beam geometry would be obtained. Moreover, the projection direction a can also be changed, that is, the position of the projection origin relative to the z axis or the axis of rotation 14. Finally, oblique projection is also possible; a ray from the projection origin to the center of the scannogram then encloses an angle other than 90° relative to the axis of rotation or the z axis. It is also possible to calculate different scannograms (also with different projection geometries) from one data set.

After the formation of a suitable scannogram in this manner, the actual CT examination can be planned on the basis of the scannogram. Notably the position and the length of the part of the examination zone to be imaged during the actual CT examination can be defined. For this subsequent examination in the step 104 a suitable value can be calculated in advance for the intensity and/or the quality of the radiation produced by the radiation source S, that is, for each individual position of the radiation source along the helical trajectory described thereby relative to the examination zone 13.

When said trajectory during the actual CT examination is identical to a part of the trajectory during the acquisition of the measured values in the step 101, the precalculation of the intensity I($\phi$,z) in the step 104 is comparatively simple. In the step 104 a value for the intensity I($\phi$,z) is derived from the set of measured values acquired in the position $\phi$,z in the step 101 and is adjusted in such a manner that an optimum compromise is reached between radiation load and image quality. The adjusted intensity is in principle higher as the absorption or attenuation of the radiation in the position $\phi$,z is stronger.

When the trajectories in the step 101 and during the subsequent CT examination do not correspond, however, for each individual position the mean attenuation can be calculated and the intensity can be preset in dependence thereon on the basis of the reconstructed 3D data set F(x,y,z) and the relevant position $\phi$,z of the radiation source.

Using the radiation intensity thus calculated and adjusted on the radiation source S, a set of measured values is acquired in the position $\phi$,z in the step 105. In the step 106 changing-over takes place to a neighboring radiation source position, and for this position a pre-calculated intensity is adjusted again in the step 104 and a further set of measured values is acquired for this adjustment and in this position. The loop 104 . . . 106 is completed a number of times until a set of measured values has been acquired for all positions on the previously defined trajectory. Subsequently, the absorption distribution can be reconstructed in the step 107. The 3D data set F'(x,y,z) resulting from this reconstruction represents the attenuation of the radiation in the region of interest (ROI). However, because of the higher intensity of the radiation during the actual CT examination, it has a significantly better signal-to-noise ratio than the attenuation values F(x,y,z) resulting from the reconstruction of the attenuation for the formation of the scannogram. The execution of the method is then terminated (block 108).

What is claimed is:

1. A computed tomography method for forming a scanogram by means of a computed tomography apparatus which includes a scanning unit for the acquisition of measured values, wherein the scanning unit is provided with a radiation source and a detector unit and is rotateable about an axis of rotation, and wherein a relative motion of the scanning unit includes a displacement relative an examination zone in a direction parallel to the axis of rotation during an acquisition of the measured values within the examination zone, the method comprising the steps of:

rotating the scanning unit about the axis of rotation during the acquisition of the measured values, reconstructing a 3D data set from the measured values which is three-dimensionally dependent on the attenuation of the radiation in the examination zone covered by the scanning unit, calculating at least one synthetic projection image from the 3D data set, calculating an attenuation of the radiation in the examination zone from the 3D data set, and controlling at least one of the quality and/or the intensity (I) of the radiation during an acquisition of measured values during a subsequent CT examination based on the attention.

2. The computed tomography method set forth in claim 1, further comprising:

determining, during a subsequent CT examination, the attenuation of the radiation in the examination zone for the individual positions ($\phi$,z) of the scanning unit relative the examination zone based on the 3D data set, and controlling the quality and/or the intensity of the ($\phi$,z)) radiation during the acquisition of measured values in the individual positions during the subsequent CT examination based on the attenuation.

3. A computed tomography apparatus for generating a scanogram via reconstruction from an acquired 3D data set, comprising:

a scanning unit which is rotatable about an axis of rotation, and provided with a radiation source and a detector unit for the acquisition of measured values, a drive device for realizing a relative motion which occurs between the scanning unit and the examination zone, such relative motion including a rotation about an axis of rotation and a displacement parallel to the axis of rotation, a reconstruction unit for conducting image processing operations including reconstructing a 3D data set from the measured values which is three-dimensionally dependent on the attenuation of the radiation in the examination zone covered by the scanning unit, calculating an attenuation of the radiation in the examination zone from the 3D data set in order to control at least one of the quality and/or the intensity (I) of the radiation during an acquisition of measured values during a subsequent CT examination based on the attention, and a control unit for controlling the scanning unit, the drive device and the reconstruction unit, wherein the control unit:

rotates about the scanning unit during the acquisition of the measured values, displaces the scanning unit parallel to the axis of rotation during the acquisition of the measured values, reconstructs from the measured values of a 3D data set which is three-dimensionally dependent on the attenuation of the radiation in the examination zone covered by the scanning unit, and calculates at least one synthetic projection image from the 3D data set.

4. The computed tomography apparatus set forth in claim 3, wherein the control unit controls scanning unit rotation and displacement simultaneously during the acquisition of the measured values, thus resulting in a helical relative motion.

5. The computed tomography apparatus set forth in claim 3, wherein the radiation beam emitted by the radiation source is shaped as a cone, and wherein the detector unit detecting the radiation beam includes a plurality of rows of detector elements which are offset relative to one another in the direction parallel to the axis of rotation.

6. A computer program for instructing a control unit to control each of: a scanning unit, a drive device and a reconstruction unit of a computed tomography apparatus to generate a scanogram by a method comprising the steps of:

rotating the scanning unit about an axis of rotation of an object to be examined during the acquisition of a set of measured values, said measured values derived by exposing the object to a radiation source and receiving an object-attenuated signal at a radiation detector, reconstructing a 3D data set from the measured values which is three-dimensionally dependent on the attenuation of the radiation in the examination zone covered by the scanning unit, calculating at least one synthetic projection image from the 3D data set, calculating an attenuation of the radiation in the examination zone from the 3D data set, and controlling at least one of the quality and/or the intensity (I) of the radiation during an acquisition of measured values during a subsequent CT examination based on the attention.

7. A computed tomography method which relies on a computed tomography apparatus comprising a scanning unit for the acquisition of measured radiation values, and provided with a radiation source and a detector unit rotatable about an axis of rotation wherein a relative motion of the scanning unit includes a displacement relative an examination zone in a direction parallel to the axis of rotation during an acquisition of the measured radiation values within the examination zone and wherein an attenuation of radiation in the examination zone, and the quality and/or intensity of the radiation is determined and controlled for individual positions of the scanning unit during CT examination based on a CT scanogram obtained by a method comprising the steps of:

rotating the scanning unit about the axis of rotation during the acquisition of the measured radiation values, reconstructing 3D data set from the measured radiation values which is three-dimensionally dependent on the attenuation of the radiation in the examination zone covered by the scanning unit, calculating the at least one synthetic projection image from the 3D data set;

calculating an attenuation of the radiation in the examination zone from the 3D data set, and controlling at least one of the quality and/or the intensity (I) of the radiation during an acquisition of measured values during a subsequent CT examination based on the attention.

* * * * *